US007309580B2

(12) United States Patent
Restaino

(10) Patent No.: US 7,309,580 B2
(45) Date of Patent: Dec. 18, 2007

(54) **CHROMOGENIC PLATING MEDIUM FOR THE RAPID PRESUMPTIVE IDENTIFICATION OF *BACILLUS ANTHRASIS*, *BACILLUS CEREUS*, AND *BACILLUS THURINGIENSIS***

(75) Inventor: Lawrence Restaino, Elburn, IL (US)

(73) Assignee: R&F Products, Inc., Downers Grove, IL (US)

( * ) Notice: Subject to any disclaimer, the term of this patent is extended or adjusted under 35 U.S.C. 154(b) by 186 days.

(21) Appl. No.: 10/188,552

(22) Filed: Jul. 5, 2002

(65) Prior Publication Data

US 2004/0005652 A1 Jan. 8, 2004

(51) Int. Cl.
*C12Q 1/04* (2006.01)
*C12N 1/20* (2006.01)

(52) U.S. Cl. .................................... 435/34; 435/253.6

(58) Field of Classification Search .................. 435/34, 435/29, 24, 23, 19, 38, 39, 40, 968, 973, 435/4, 253.6
See application file for complete search history.

(56) References Cited

U.S. PATENT DOCUMENTS 6,284,517 B1 * 9/2001 Restaino .................. 435/252.4
6,558,917 B2 * 5/2003 Schabert ...................... 435/34
6,660,494 B2 * 12/2003 Schabert et al. .............. 435/34
6,764,832 B2 * 7/2004 Restaino ...................... 435/34
2003/0032080 A1 * 2/2003 Schabert ...................... 435/34
2004/0005652 A1 * 1/2004 Restaino ...................... 435/34

OTHER PUBLICATIONS

Mossel et al, "Applied Microbiology", vol. 15(3), pp. 650-653, (May 1967).*
Slein et al, "J. Bacteriology", vol. 90 (1), pp. 69-81, (Jul. 1965).*
Kniseley, "J. Bacteriology", vol. 92 (3), pp. 1778-1783, (Sep. 1966).*
Volwerk et al, J. Cellular Biochem., vol. 39, pp. 315-325, (1989).*
Manafi, M, International J. Food Micro., vol. 60, pp. 205-218, (2000).*
Cole et al, J. Clinical Microb., vol. 19, No. 1, pp. 48-53, (1984).*

* cited by examiner

*Primary Examiner*—Jon Weber
*Assistant Examiner*—Kailash C. Srivastava
(74) *Attorney, Agent, or Firm*—Marshall A. Bumeister

(57) ABSTRACT

A plating medium for the presumptive identification of *Bacillus cereus, Bacillus thuringiensis* and/or *Bacillus anthrasis* that includes a nutrient base to facilitate growth of *Bacillus cereus, Bacillus thuringiensis* and *Bacillus anthrasis*, a chromogenic substrate that changes color responsive to the presence of PC-PLC enzymes, and an ingredient that promotes the expression of the PC-PLC enzyme. In a preferred embodiment, the medium includes a second chromogenic substrate that changes color responsive to the presence of PI-PLC enzymes and an ingredient that promotes the expression of the PI-PLC enzyme.

13 Claims, No Drawings

CHROMOGENIC PLATING MEDIUM FOR THE RAPID PRESUMPTIVE IDENTIFICATION OF *BACILLUS ANTHRASIS*, *BACILLUS CEREUS*, AND *BACILLUS THURINGIENSIS*

The present invention relates to the rapid identification of *Bacillus anthrasis*, *Bacillus cereus*, and *Bacillus thuringiensis* using a chromogenic plating medium. It also relates to the differentiation of *Bacillus anthrasis* from *Bacillus cereus*, and *Bacillus thuringiensis*.

BACKGROUND OF THE INVENTION

Although *B. anthrasis* (anthrax), *B. cereus* (foodborne gastrointestinal disease), and *B. thuringiensis* (biological pesticide) produce a variety of pathological effects, the three bacilli are related genetically with some authors placing these organisms as subspecies of the group *Bacillus cereus* (Turnbull, P.C.B.1999. Definitive identification of *Bacillus anthrasis*-a review, Journal of Applied Microbiology, Vol. 87 pages 237-240; Helgason, E. et al. 2000. *Bacillus anthrasis*, *Bacillus cereus*, and *Bacillus thuringiensis*-one species on the basis of genetic evidence, Applied and Environmental Microbiology, Vol. 66 pages 2627-2630). An easy and rapid separation of these three bacterial strains is important for determining the causative agent of a pathological effect, especially with regards to the potential use of *B. anthrasis* as a biological weapon.

Traditionally, *Bacillus cereus/Bacillus thuringiensis* have been presumptively isolated from a variety of sources including foods and the environment using mannitol egg yolk polymyxin agar (MYP) dependent on expression of lecithinase activity, fermentation of mannitol and resistance to polymyxin (Compendium of Methods for the Microbiological Examination of Foods, 1992, Chapter 35, American Public Health Association). With the shortcomings of MYP involving frequent false positive and negative reactions and coalescing of colonies causing difficulty in colony enumeration, in 2001 a plating medium using 5-bromo-4-chloro-3-indoxyl myo-inositol-1-phosphate to detect phosphatidylinositol-specific phospholipase C (PI-PLC) in *B. cereus/B. thuringiensis* producing turquoise colonies was developed and patented (Peng, H. et al. 2001. Isolation and enumeration of *Bacillus cereus* from foods on a novel chromogenic plating medium, Food Microbiology, Vol. 18 pages 231-238; Restaino, L. 2001. Plating media for the presumptive identification of *Bacillus cereus* and *Bacillus thuringiensis*, U.S. Pat. No. 6,284,517). For *B. anthrasis*, blood agar containing polymyxin B with incubation at 37° C. for 24 hours has traditionally been used resulting in a large percentage of false positive isolates.

Although *B. cereus*, *B. thuringiensis*; and *B. anthrasis* produce PI-PLC, the molecular weight of this enzyme is different in *B. anthrasis* compared with the enzyme produced by the other two bacilli indicating a different mechanism of action (Guttmann, D. M. and D. J. Ellar. 2000. Phenotypic and genotypic comparisons of 23 strains from the *Bacillus cereus* complex for a selection of known and putative *B. thuringiensis* virulence factors, FEMS Microbiology Letters, Vol. 188 pages 7-13). This reaction can be demonstrated on plating medium containing the chromogenic substrate 5-bromo-4-chloro-3-indoxyl-myo-inositol-1-phosphate where after incubation *B. cereus* and *B. thuringiensis* produce turquoise colonies and *B. anthrasis* yield white colonies. However, phosphatidylcholine-specific phospholipase C (PC-PLC) enzyme is identical in *B. cereus*, *B. thuringiensis* and *B. anthrasis*, but the rate of production is slower for *B. anthrasis* (Guttmann, D. M. and D. J. Ellar. 2000. Phenotypic and genotypic comparisons of 23 strains from the *Bacillus cereus* complex for a selection of known and putative *B. thuringiensis* virulence factors, FEMS Microbiology Letters, Vol. 188 pages 7-13).

SUMMARY OF THE INVENTION

It is a principle object of the present invention to provide a single plating medium with a chromogenic system for the presumptive identification of *Bacillus cereus*, *Bacillus thuringiensis* and *Bacillus anthrasis* from a mixed sample. It is also an object of this invention to differentiate *Bacillus anthrasis* from *Bacillus cereus* and *Bacillus thuringiensis*.

The inventor realizes that when *B. cereus*, *B. thuringiensis*, and *B. anthrasis* are inoculated in a growth medium and allowed to incubate at an optimal temperature for a required length of time, these bacterial strains will produce identical PC-PLC, whereas, the PI-PLC from *B. anthrasis* will differ from the PI-PLC from the other two bacilli. Therefore, it is an object of the present invention to produce a plating medium for the presumptive isolation of *B. cereus*, *B. thuringiensis*, and *B. anthrasis* that has at least one chromogenic substrate for the identification of PI-PLC and/or PC-PLC. The inventor realizes that a chromogenic substrate (i.e., 5-bromo-4-chloro-3-indoxyl-myo-inositol-1- phosphate) for PI-PLC will identify this enzyme in *B. cereus* and *B. thuringiensis*—(produce turquoise colonies) but not *B. anthrasis* (produce white to cream colonies) and it is the purpose of this invention to use a chromogenic substrate (i.e., 5-bromo-6-chloro-3-indoxyl-choline-phosphate) for PC-PLC alone or in conjunction with a chromogenic substrate for PI-PLC to differentiate *B. anthrasis* from *B. cereus* and *B. thuringiensis*.

The inventor has found that the enzymes PI-PLC and PC-PLC produce little reaction to the substrates presently available in the absence of an ingredient that promotes the expression of these enzymes. Hence, a plating medium according to the present invention comprises a nutrient base that promotes the growth of *B. cereus*, *B. thuringiensis*, and *B. anthracis* under incubating conditions, at least one chromogenic substrate detecting PC-PLC with or without at least one chromogenic substrate identifying PI-PLC, and at least one ingredient that promotes the expression of the enzymes reacting with the chromogenic substrates.

In practice, the plating medium according to the present invention comprises (1) a nutrient medium that promotes the growth of *B. cereus*, *B. thuringiensis*, and *B. anthrasis* under incubating conditions, (2) at least one ingredient that promotes repair of injured bacilli cells under incubating conditions, (3) at least one ingredient that inhibits the growth of most bacilli other than *B. cerceus*, *B. thuringiensis*, and *B. anthrasis* and other related and unrelated bacteria under incubating conditions, (4) at least one ingredient that inhibits the growth of yeasts and molds under incubating conditions, (5) at least one chromogenic substrate detecting PC-PLC with or without at least one chromogenic substrate identifying PI-PLC, (6) at least one ingredient that promotes the expression of the enzymes reacting with the chromogenic substrates, and (7) at least one ingredient that solidifies the mixture.

DETAILED DESCRIPTION OF THE INVENTION

It is necessary that *B. cereus, B. thuringiensis,* and *B. anthrasis* consume nutrients and grow in order for the bacteria to secrete the sought after enzymes, therefore, the plating medium must have a rich nutrient base. In order to promote the growth of the sought after bacterial strains, the plating medium of the present invention includes one or more of the ingredients casein digest, soytone, proteose peptone, Lab Lemco (meat extract) powder, and yeast extract. In the preferred medium described throughout this specification, casein digest, Lab Lemco powder and soytone are in the plating medium and form the nutrient base.

The preferred plating medium includes sodium pyruvate to facilitate the repair of injured bacilli cells.

In any selective plating medium, the growth of bacteria cells other than the sought after bacterial species complicates or can confuse the reading of the plates; therefore, it is desirable to inhibit the growth of bacterial species other than the desired bacterial species. The medium of the present invention must suppress most bacteria and Bacillus species other than *B. cereus, B. thuringiensis,* and *B. anthrasis.* For this purpose, the media of the present invention preferably contain one or more of the ingredients: lithium chloride, ceftazidime pentahydrate, polymyxin B sulfate, third or fourth generation cephalosporins, and moxalactam. The preferred plating medium contains lithium chloride, ceftazidime pentahydrate, and polymyxin B sulfate. Also, the preferred medium contains cycloheximide to inhibit the growth of yeasts and molds.

In the preferred embodiment, the chromogenic substrate that changes color responsive to the presence of PC-PLC is 5-bromo-4-chloro-3-indoxyl-choline-phosphate. With this chromogenic substrate identifying PC-PLC, *B. cereus* and *B. thuringiensis* can be isolated from *B. anthrasis* by discerning differences in the rates of enzyme expression. Other suitable chromogenic substrates identifying PC-PLC are 3-Indoxyl-choline phosphate, 5-Bromo-6-chloro-3-indoxyl-choline phosphate, 6-Chloro-3-indoxyl-choline phosphate, 5-Iodo-3-indoxyl -choline phosphate, N-Methylindoxyl-choline phosphate, 2-Nitrophenyl-choline phosphate, 3-Nitrophenyl-choline phosphate, and 4-Nitrophenyl-choline phosphate.

In addition, a second chromogenic substrate is preferably added to the plating medium identifying the PI-PLC enzyme. With two chromogenic substrates identifying PC-PLC and PI-PLC incorporated in the preferred plating medium, after incubation, the *B. cereus* and *B. thuringiensis* colonies will display a third color resulting from enzymatic reactions on the two chromogens; whereas, the color of the *B. anthrasis* colonies will result from the chromogenic substrate identifying PC-PLC only.

Ingredients that promote the expression of the PC-PLC and PI-PLC enzymes in the plating medium are bovine serum, silicates, and manganese chloride (or other manganese containing compounds). Table 1 presents the salts of various divalent cations versus the expression of PC-PLC in the presence of 5-bromo-4-chloro-3-indoxyl-choline-phosphate. After incubation at 37 ° C., the only divalent cation that produced blue or turquoise colonies was manganese chloride. After 48 hours, B. cereus and B. thuringiensis produced turquoise colonies with a narrow rim, whereas, B. anthracis yielded a cream color colony with a blue dot in the center of the colony. In the preferred embodiment, the ingredients that promote the expression of the PC-PLC and PI-PLC enzymes are bovine serum and manganese chloride.

TABLE 1

EFFECT OF VARIOUS MINERAL CATIONS ON THE EXPRESSION OF PHOSPHATIDYLCHOLINE-SPECIFIC PHOSPHOLIPASE C IN *BACILLUS CEREUS*, *BACILLUS THURINGIENSJS* AND *BACILLUS ANTHRASIS* INCUBATED AT 37° C. FOR 24 AND 48 HOURS

| Mineral Cations | *Bacillus thuringiensis* ATCC 10792 Colonial Morphologies | | *Bacillus cereus* ATCC 14579 Colonial Morphologies | | *Bacillus anthrasis* AMES-RIID and ANR-1 Colonial Morphologies | |
|---|---|---|---|---|---|---|
|  | 24 hours | 48 hours | 24 hours | 48 hours | 24 hours | 48 hours |
| No added cations | Large cream colored | Large cream colored | Large cream colored | Large cream colored | Small cream colored | Medium cream colored |
| 0.1% Manganese chloride | Turquoise with white rim | Turquoise with white rim | Turquoise with white rim | Turquoise with white rim | Small cream colored | Cream with blue center |
| 0.12% Magnesium sulfate | Large cream colored | Large cream colored | Large cream colored | Large cream colored | Small cream colored | Medium cream colored |
| 0.074% Calcium chloride | Large cream colored | Large cream colored | Large cream colored | Large cream colored | Small cream colored | Medium cream colored |
| 0.015% Zinc sulfate | Large cream colored | Large cream colored | Large cream colored | Large cream colored | Small cream colored | Medium cream colored |
| 0.078% Cupric sulfate | Small colorless | Small colorless | Small colorless | Small colorless | No growth to small colorless | No growth to small colorless |

An ingredient must be added to the mixture to solidify the mixture. In the preferred composition, this ingredient is agar.

The formula for the preferred embodiment of the plating medium is present in Table 2.

TABLE 2

FORMULA FOR THE PREFERRED EMBODIMENT OF THE PLATING MEDIUM

| Chemical | Supplier | Grams/liter |
|---|---|---|
| Casein Digest | Difco | 15.00 |
| Lab Lemco Powder | Oxoid | 5.00 |
| Soytone | Difco | 5.00 |
| Sodium pyruvate | Biosynth | 10.00 |
| Tween 80 (polyoxyethylenesorbitan monooleate | — | 0.5 |
| Sodium chloride | — | 5.0 |
| Manganese chloride tetrahydrate | — | At least 1.0 grams |
| Cycloheximide | — | 0.20 |
| Lithium chloride | Sigma | 2.00 |
| Agar | Difco | 15.00 |
| Bovine serum 82-067 | Serologicals | 3.20 |
| Ceftazidime pentahydrate | Glaxo Wellcome | 0.04 |
| 5-bromo-4-chloro-3 indoxyl-choline phosphate or other chromogenic or fluorogenic substrates* | Biosynth | 0.32 |
| Polymyxin B sulfate | Sigma | 100,000 units |

*In addition, chromogenic substrates such as 5-bromo-4-chloro-3-indoxyl-myo-inositol-1-phosphate or fluorogenic substrates that detect PI-PLC may be added to the plating medium at a minimum concentration of 0.30 grams/liter.

Prior to the preparation of the selective/differential plating medium, all of the heat resistant ingredients are mixed into a vessel containing 970 ml of deionized/distilled water. The mixture should be warmed slightly and stirred to dissolve any clumps and powder. The pH of the mixture should be recorded within a range of 6.80 to 7.20. The plating medium is sterilized at 121-124° C. for 15 minutes. After sterilization, the medium is cooled in a water bath at 50° C. Thereafter, one at a time, the heat sensitive ingredients, including the chromogenic substrate(s), bovine serum, ceftazidime pentahydrate, and polymyxin B sulfate, are added to 30 ml of deionized/distilled water and dissolved, hereafter referred to as the supplement. The supplement is filter-sterilized and poured into the cooled sterile plating medium. The completed medium is swirled and the composition is placed in Petri dishes and stored under proper conditions overnight. The final pH of the plating medium is 6.80 to 7.20. The plating medium is stable up to 60 days stored in a plastic sleeve at 4-8° C.

EXAMPLE I

The bacterial strains indicated in Table 3 were applied to the Petri dishes referred to above (using only the 5-bromo-4-chloro-3-indoxyl-choline phosphate chromogenic substrate), and incubated at 35-37° C. for a period of 48 hours. Thereafter, the surfaces of the plating medium in the Petri dishes were observed, and produced the following results presented in Table 3.

TABLE 3

COLONIAL MORPHOLOGIES OF VARIOUS BACTERIAL STRAINS ON THE PLATING MEDIUM AT 35-37° C. FOR 48 HOURS

| Bacteria | Number of strains | Colonial Morphologies |
|---|---|---|
| *Bacillus cereus* | 7 | Teal flat dull colonies with white rim |
| *Bacillus thuringiensis* | 5 | Teal flat dull colonies with white rim |
| *Bacillus anthrasis* | 2 | Cream flat dull colonies with blue dot in the center |
| *Bacillus circulans* | 1 | White domed dull colonies |
| *Bacillus megaterium*, *Bacillus licheniformis*, *Bacillus subtilis*, *Bacillus brevis*, *Bacillus lentus*, *Bacillus pumilus*, *Bacillus spaericus*, *Bacillus mycoides* and, *Bacillus insolitus* | 1 strain each | No growth |
| *PaeniBacillus macerans*, and *PaeniBacillus polymyxa* | 1 strain each | No growth |
| *Listeria monocytogenes* | 3 | No growth to white pinpoint domed colonies |
| *Listeria ivanovii*, *Listeria innocua*, *Listeria seeligeri*, and *Listeria welshmeri* | 1 strain each | White domed colonies; pinpoint to <1 mm |
| *Enterococcus faecium* | 4 | No growth to white domed colonies; pinpoint |
| *Enterococcus faecalis* | 2 | No growth to white domed colonies; pinpoint |
| *Enterococcus avium* | 3 | No growth |
| *Staphylococcus aureus* | 5 | No growth |
| *Micrococcus* sp., *Pediococcus cerevisiae*, *Staphylococcus epidermidis*, and *Staphylococcus saprophyticus* | 1 strain each | No growth |
| Gram negative species* | 7 | No growth |

*One strain each of *Pseudomonas aeruginosa*, *Escherichia coli*, *Enterobacter agglomerans*, *Salmonella derby*, *Salmonella typhimurium*, *Klebsiella pneumoniae*, and *Escherichia coli* O157:H7.

From Table 3 it is obvious that *B. cereus*/*B. thuringiensis* produce a teal colored colony that is easily distinguished from the *B. anthrasis* colonies which are cream flat dull with a blue dot center. The growth of other PC-PLC producing bacteria are inhibited by the plating medium, and are eliminated as potential false positives. Any other non producing PC-PLC bacteria growing on the plating medium will form white colored colonies.

EXAMPLE 2

A second set of Petri dishes were prepared as indicated above, except a second chromogenic substrate (5-bromo-4-chloro-3-indoxyl-myo-inositol-1-phosphate) was added to the mixture with the first chromogenic substrate. The bacterial strains indicated in Table 3 were applied to the second set of Petri dishes (using both the 5-bromo-4-chloro-3-indoxyl-choline phosphate chromogenic substrate and the 5-bromo-4-chloro-3-indoxyl-myo-inositol-1-phosphate substrate), and incubated at 35-37° C. for a period of 48 hours. Thereafter, the surfaces of the plating medium in the second set of Petri dishes were observed. *Bacillus anthrasis* colonies were observed to be substantially the same as set forth in Table 3, namely, cream flat dull colonies with a blue dot in the center. However, the *Bacillus cereus* and *Bacillus thuringiensis* colonies appeared with a color that is a blend of the colors of the two substrates (blue and turquoise, respectively), namely, bluish-turquoise.

Although variations in the plating medium of the preferred embodiment are set forth above, other variations will become apparent to those skilled in the art. It is therefore intended that this invention be not limited to the foregoing specification, but rather only to the appended claims.

The invention claimed is:

1. A plating medium for the presumptive identification of *Bacillus cereus, Bacillus thuringiensis* and/or *Bacillus anthracis* comprising a nutrient base to facilitate growth of *Bacillus cereus, Bacillus thuringiensis* and/or *Bacillus anthracis*, a first-chromogenic substrate that changes the color of the medium to a first color responsive to the presence of phosphatidylcholine-specific phospholipase C (PC-PLC) enzymes, and a second chromogenic substrate that changes the color of the medium to a second color responsive to the presence of phosphatidylinositol-specific phospholipase C (PI-PLC) enzymes of *Bacillus thuringiensis* and *Bacillus cereus*, the first and second colors being different and blending to a third color, the first, second and third colors contrasting with each other and with the color of the medium.

2. The plating medium of claim 1 for the presumptive identification of *Bacillus cereus, Bacillus thuringiensis* and/or *Bacillus anthracis* and at least one ingredient that promotes the expressions of the PC-PLC and PI-PLC enzymes.

3. The plating medium of claim 1 for the presumptive identification of *Bacillus cereus, Bacillus thuringiensis* and/or *Bacillus anthracis* in combination with an ingredient to suppress the growth of bacteria other than *Bacillus cereus, Bacillus thuringiensis* and *Bacillus anthracis*.

4. The plating medium of claim 3 for the presumptive identification of *Bacillus cereus, Bacillus thuringiensis* and/or *Bacillus anthracis*, wherein the ingredient to suppress the growth of bacteria other than *Bacillus cereus, Bacillus thuringiensis* and *Bacillus anthracis* is one or more members selected from the group consisting of lithium chloride, ceftazidime pentahydrate, polymyxin B sulfate, third or fourth generation cephalosporins, and moxalactam.

5. The plating medium for the presumptive identification of *Bacillus cereus, Bacillus thuringiensis* and/or *Bacillus anthracis* comprising a nutrient base to facilitate growth of *Bacillus cereus, Bacillus thuringiensis* and *Bacillus anthracis*, a first-chromogenic substrate that changes the color of the medium to a first color responsive to the presence of phosphatidyicholine-specific phospholipase C (PC-PLC) enzymes, and a second chromogenic substrate that changes the color of the medium to a second color responsive to the presence of phosphatidylinositol-specific phospholipase C (PI-PLC) enzymes of *Bacillus thuringiensis* and *Bacillus cereus*, the first and second colors being different and blending to a third color, the first, second and third colors contrasting with each other and with the color of the medium, wherein the first chromogenic substrate that changes color responsive to the presence of PC-PLC enzymes is selected from the group consisting of 5 -bromo-4-chloro-3 -indoxyl-choline phosphate, 3-indoxyl-choline phosphate, 5-bromo-6-chloro-3indoxyl-choline phosphate, 6-chloro-3-indoxyl-choline phosphate, 5 -iodo-3-indoxyl-choline phosphate, N-methylindoxyl-choline phosphate, 2-nitrophenyl-choline phosphate, 3-nitrophenyl-choline phosphate, and 4-nitrophenyl-choline phosphate.

6. The plating medium of claim 1 for the presumptive identification of *Bacillus cereus, Bacillus thuringiensis* and/or *Bacillus anthracis*, wherein the second chromogenic substrate that changes color responsive to the presence of PI-PLC enzymes is 5-bromo-4-chloro-3-indoxyl-myo-inositol-1-phosphate.

7. The plating medium of claim 1 for the presumptive identification of *Bacillus cereus, Bacillus thuringiensis* and/or *Bacillus anthracis*, wherein the first chromogenic substrate that changes color responsive to the presence of PC-PLC enzymes is 5-bromo-4-chloro-3-indoxyl-choline phosphate, and the second chromogenic substrate that changes color responsive to the presence of PI-PLC enzymes is 5-bromo-4-chloro-3-indoxyl-myo-inositol-1-phosphate.

8. The plating medium of claim 1 for the presumptive identification of *Bacillus cereus, Bacillus thuringiensis* and/or *Bacillus anthracis* and an ingredient in the plating medium that promotes the expression of the PC-PLC and PI-PLC enzymes, said ingredient is selected from the group consisting of bovine serum, silicates, Tween®, manganese chloride, manganese acetate tetrahydrate, manganese nitrate tetrahydrate, and manganese sulfate monohydrate.

9. The plating medium of claim 1 for the presumptive identification of *Bacillus cereus, Bacillus thuringiensis* and/or *Bacillus anthracis*, wherein the nutrient base to facilitate growth of *Bacillus cereus, Baclllus thuringiensis* and *Bacillus anthracis* comprises at least one member selected from the group consisting of casein digest, soytone, proteose peptone, meat extract powder, and yeast extract.

10. The plating medium of claim 1 for the presumptive identification of *Bacillus cereus, Bacillus thuringiensis* and/or *Bacillus anthracis* in combination with at least one ingredient to repair injured *Bacilli* cells.

11. The plating medium of claim 10 for the presumptive identification of *Bacillus cereus, Bacillus thuringiensis* and/or *Bacillus anthracis*, wherein the ingredient to repair injured *Bacilli* cells is sodium pyruvate.

12. The plating medium of claim 1 for the presumptive identification of *Bacillus cereus, Bacillus thuringiensis* and/or *Bacillus anthracis* and at least one ingredient to solidify the mixture.

13. The plating medium for the presumptive identification of *Bacillus cereus, Bacillus thuringiensis* and/or *Bacillus anthracis* comprising: a nutrient base comprising one or more members selected from the group consisting of casein digest, soytone, proteose peptone, meat extract powder, and yeast extract; a first chromogenic substrate consisting of 5-bromo-4-chloro-3-indoxyl-choline phosphate that changes the color of the medium to a first color responsive to the presence of phosphatidylcholine-specific phospholipase C (PC-PLC); a second chromogenic substrate consisting of 5-bromo-4-chloro-3-indoxyl-myo-inositol-1-phosphate that changes the color of the medium to a second color responsive to the presence of phosphatidylinositol~specific phospholipace C (PI-PLC) enzymes in *Bacillus thuringiensis* and *Bacillus cereus*; wherein the first and second colors blending to a third color, said first, second and third colors contrasting with each other and with the color of the medium; an ingredient that promotes the expression of the PC-PLC and PI-PLC enzymes comprising one or more members selected from the group consisting of bovine serum, silicates, Tween®, manganese chloride, manganese acetate tetrahydrate, manganese nitrate tetrahydrate, and manganese sulfate monohydrate; and agar to solidify the mixture.

* * * * *